US008148394B2

(12) United States Patent
Edwards et al.

(10) Patent No.: US 8,148,394 B2
(45) Date of Patent: Apr. 3, 2012

(54) AZAINDOLES HAVING SEROTONIN RECEPTOR AFFINITY

(75) Inventors: Louise Edwards, Mississauga (CA); Abdelmalik Slassi, Mississauga (CA); Ashok Tehim, Ridgewood, NJ (US); Tao Xin, Toronto (CA)

(73) Assignee: NPS Pharmaceuticals, Inc., Bedminster, NJ (US)

( * ) Notice: Subject to any disclaimer, the term of this patent is extended or adjusted under 35 U.S.C. 154(b) by 625 days.

(21) Appl. No.: 11/835,325

(22) Filed: Aug. 7, 2007

(65) Prior Publication Data

US 2008/0004307 A1 Jan. 3, 2008

Related U.S. Application Data

(62) Division of application No. 11/165,122, filed on Jun. 24, 2005, now Pat. No. 7,268,127, which is a division of application No. 10/739,302, filed on Dec. 19, 2003, now Pat. No. 6,916,818, which is a division of application No. 09/636,592, filed on Aug. 10, 2000, now Pat. No. 6,686,374.

(60) Provisional application No. 60/148,343, filed on Aug. 12, 1999.

(51) Int. Cl.
*A01N 43/42* (2006.01)
*A61K 31/44* (2006.01)
*C07D 221/02* (2006.01)
(52) U.S. Cl. ....................... 514/300; 546/112
(58) Field of Classification Search ............ None
See application file for complete search history.

(56) References Cited

OTHER PUBLICATIONS

Dorwald F. A. Side Reactions in Organic Synthesis, 2005, Wiley: VCH, Weinheim p. IX of Preface.*
Vippagunta et. al. Advanced Drug Delivery Reviews 48 (2001) 3-26.*
Schaffhauser, et. al., Biochemical Pharmacology, 78(8), 2009, 1035-1042.*
http://www.medpagetoday.com/Neurology/AlzheimersDisease/18794 (last accessed Aug. 23, 2010).*

* cited by examiner

*Primary Examiner* — Jeffrey Murray
(74) *Attorney, Agent, or Firm* — Stoel Rives LLP

(57) ABSTRACT

Described herein are compounds with affinity for the $5\text{-}HT_6$ receptor, which have the general formula I:

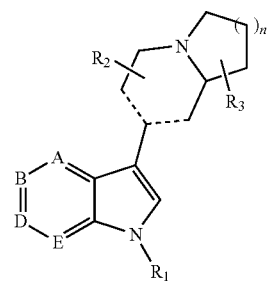

Formula 1 wherein A, B, D, E, $R_1$ to $R_3$ and n are described herein. Also described is the use of these compounds as pharmaceuticals to treat indications where inhibition of the $5\text{-}HT_6$ receptor is implicated, such as schizophrenia.

16 Claims, No Drawings

AZAINDOLES HAVING SEROTONIN RECEPTOR AFFINITY

This application is a divisional of U.S. application Ser. No. 11/165,122, filed Jun. 24, 2005, allowed, which is a divisional of U.S. application Ser. No. 10/739,302, filed Dec. 19, 2003, and issued as U.S. Pat. No. 6,916,818 on Jul. 12, 2005, which is a divisional of U.S. application Ser. No. 09/636,592, filed Aug. 10, 2000 and issued as U.S. Pat. No. 6,686,374 on Feb. 3, 2004, which claims the benefit of U.S. Provisional Application Ser. No. 60/148,343, filed Aug. 12, 1999. The disclosures of the above applications are hereby incorporated by reference in their entirety.

This invention relates to azaindole compounds having affinity for serotonin receptors, to pharmaceutical and diagnostic compositions containing them and to their medical use, particularly in the diagnosis and treatment of CNS conditions.

According to one aspect of the invention, there are provided compounds of Formula I and a salt, solvate of hydrate thereof:

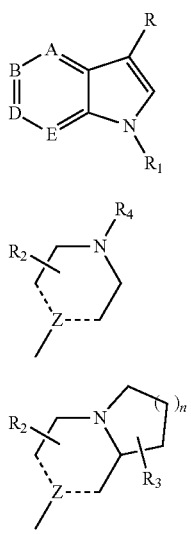

wherein:
R represents a group of Formula II or Formula III; one of A, B D or E is a N atom, the remainder being CH groups;
$R_1$ is selected from the group consisting of $SO_2Ar$, $C(O)Ar$, $CH_2 Ar$ and $Ar$;
$R_2$, $R_3$ and $R_4$ are independently selected from the group consisting of H and alkyl;
---represents a single or double bond, with the proviso that there is only one double bond in the ring at a time;
n is an integer of from 1-3;
Z is selected from the group consisting of C, CH and N, provided that when ---is a double bond, Z is C and when ---is a single bond, Z is selected from CH and N; Ar is an optionally substituted aryl group;
Ar is an optionally substituted aryl group;
with the proviso that when R is a group of Formula II, $R_1$ is $SO_2Ar$.

It is an aspect of the invention to provide compounds which bind to the 5-$HT_6$ receptor.

Certain compounds of the invention also bind to the 5-$HT_7$ receptor, and a further object of the invention provides such compounds having mixed 5-$HT_6$ and 5-$HT_7$ activity.

According to another aspect of the invention, there are provided pharmaceutical compositions comprising a compound of Formula I, in an amount effective to antagonize the 5-$HT_6$ receptor, and a pharmaceutically acceptable carrier.

In another aspect of the invention there are provided compositions containing a compound of Formula I, in amounts for pharmaceutical use, to treat CNS conditions where a 5-$HT_6$ antagonist is indicated, for example, for the treatment or prevention of central nervous system disturbances such as psychosis, schizophrenia, manic depression, depression, neurological disturbances, memory disturbances, Parkinsonism, amylotrophic lateral sclerosis, Alzheimer's disease and Huntington's disease.

In another aspect of the invention, there are provided compounds useful as intermediates in the preparation of a compound of Formula I, and having a general structure according to Formula IV:

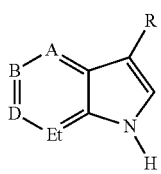

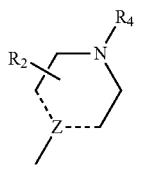

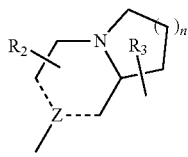

wherein
R represents a group of Formula II or Formula III;
one of A, B D or E is a N atom, the remainder being CH groups;
$R_2$, $R_3$ and $R_4$ are independently selected from the group consisting of H and alkyl;
---represents a single or double bond, with the proviso that there is only one double bond in the ring at a time;
n is an integer of from 1-3;
Z is selected from the group consisting of C, CH and N, provided that when ---is a double bond, Z is C and when ---is a single bond, Z is selected from CH and N.

These and other aspects of the present invention are described in greater detail hereinbelow.

DETAILED DESCRIPTION AND PREFERRED EMBODIMENTS

The term "alkyl" as used herein means straight and branched chain alkyl radicals containing from one to six carbon atoms and includes methyl, ethyl, propyl, isopropyl, t-butyl and the like.

The term "alkoxy" as used herein means straight and branched chain alkoxy radicals containing from one to six carbon atoms and includes methoxy, ethoxy, propyloxy, isopropyloxy, t-butoxy and the like.

The term "aryl" as used herein means an optionally substituted 5-10 membered mono- or bi-cyclic aromatic group which can contain up to 2 heteroatoms, wherein the optional substituents are independently selected from 1-4 members of the group consisting of halo, hydroxy, alkyl, alkoxy, thioalkyl, trifluoromethyl and trifluoromethoxy, and includes phenyl, naphthyl, indanyl, indolyl, quinolyl, furyl, thienyl and the like.

The term halo as used herein means halogen and includes fluoro, chloro, bromo, iodo and the like, in both radioactive and non radioactive forms.

The term "pharmaceutically acceptable salt" means an acid addition salt which is compatible with the treatment of patients.

A "pharmaceutically acceptable acid addition salt" is any non-toxic organic or inorganic acid addition salt of the base compounds represented by Formula I. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tri-carboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid and other sulfonic acids such as methanesulfonic acid and 2-hydroxyethanesulfonic acid. Either the mono- or di-acid salts can be formed, and such salts can exist in either a hydrated, solvated or substantially anhydrous form. In general, the acid addition salts of a compound of Formula I are more soluble in water and various hydrophilic organic solvents, and generally demonstrate higher melting points in comparison to their free base forms. The selection criteria for the appropriate salt will be known to one skilled in the art. Other non-pharmaceutically acceptable salts, e.g. oxalates, may be used for example in the isolation of compounds of Formula I for laboratory use, or for subsequent conversion to a pharmaceutically acceptable acid addition salt. It should be noted that compounds of Formula I wherein Z is N are not stable in the presence of strong acid (for example 1N HCl), therefore when preparing acid addition salts of such compounds, care must be taken to select an appropriately mild acid, for example citric acid.

"Solvate" means a compound of Formula I, or the pharmaceutically acceptable salt of a compound of Formula I, wherein molecules of a suitable solvent are incorporated in a crystal lattice. A suitable solvent is physiologically tolerable at the dosage administered as the solvate. Examples of suitable solvents are ethanol, water and the like. When water is the solvent, the molecule is referred to as a hydrate.

The term "stereoisomers" is a general term for all isomers of the individual molecules that differ only in the orientation of their atoms in space. It includes mirror image isomers (enantiomers), geometric (cis/trans) isomers and isomers of compounds with more than one chiral centre that are not mirror images of one another (diastereomers).

The term "treat" or "treating" means to alleviate symptoms, eliminate the causation of the symptoms either on a temporary or permanent basis, or to prevent or slow the appearance of symptoms of the named disorder or condition.

The term "therapeutically effective amount" means an amount of the compound which is effective in treating the named disorder or condition.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

The term "schizophrenia" means schizophrenia, schizophreniform disorder, schizoaffective disorder and psychotic disorder wherein the term "psychotic" refers to delusions, prominent hallucinations, disorganized speech or disorganized or catatonic behavior. See Diagnostic and Statistical Manual of Mental Disorder, fourth edition, American Psychiatric Association, Washington, D.C.

The present invention includes within its scope prodrugs of the compounds of Formula I. In general, such prodrugs will be functional derivatives of the compounds of Formula I which are readily convertible in vivo into the required compound of Formula I. Conventional procedures for the selection and preparation of suitable prodrug derivatives are described, for example, in "Design of Prodrugs" ed. H. Bundgaard, Elsevier, 1985.

Compounds of Formula I include those in which $R_1$ is selected from the group consisting of $SO_2Ar$, $C(O)Ar$, $CH_2Ar$ and Ar, wherein Ar is an optionally substituted aryl group. Preferably, $R_1$ is an $SO_2Ar$ group or a $C(O)Ar$ group. More preferably, $R_1$ is an $SO_2Ar$ group. Preferably Ar is selected from substituted phenyl and naphthyl, more preferably alkyl- or halo-substituted phenyl or naphthyl. Most preferably, Ar is a naphthyl group.

When R is a group of Formula II, $R_2$ and $R_4$ are preferably H or alkyl. More preferably, $R_2$ is H and $R_4$ is methyl. Further, in preferred embodiments of Formula II Z is a carbon-containing group. In more preferred embodiments, Z is C and one of ---- represents a double bond. Specifically, Formula II represent a group such as 1-methyl-1,2,5,6-tetrahydro-pyridin-4-yl or 1-methyl-piperidin-4-yl.

Compounds of Formula I include those in which R is a group of Formula III. Preferably n is 1 or 2. Again, Z is, preferably, a carbon-containing group. More preferably, Z is C and one of ---- represents a double bond. Preferably $R_2$ and $R_3$ are H or alkyl, more preferably both are H. Specifically, Formula III represents a group such as 1,2,3,5,8,8a-hexahydro-7-indolizinyl, octahydro-7-indolizinyl, 1,6,7,8,9,9a-hexahydro-4-quinolizinyl or octahydro-2-quinolizinyl.

In a further embodiment of the invention, compounds of Formula I encompass those in which halo is selected from non-radioactive halo and radioactive halo. When halo is radioactive halo, it may be, for example, radioactive iodo.

Specific embodiments of Formula I include:
3-(1,2,3,5,8,8a-Hexahydro-7-indolizinyl)-1H-4-azaindole;
3-(Octahydro-7-indolizinyl)-1H-4-azaindole;
3-(Octahydro-7-indolizinyl)-1-(1-naphthalenesulfonyl)-4-azaindole;
3-(Octahydro-7-indolizinyl)-1-(2-naphthalenesulfonyl)-4-azaindole;
3-(Octahydro-7-indolizinyl)-1-(2-naphthalenesulfonyl)-4-azaindole;
1-(2,6-Dichlorobenzoyl)-3-(1,2,3,5,8,8a-hexahydro-7-indolizinyl)-5-azaindole;
1-(2,6-Dichlorobenzoyl)-3-(1-methyl-1,2,3,6-tetrahydro-4-pyridinyl)-5-azaindole;
1-(2,6-Dichlorobenzoyl)-3-(1-methyl-4-piperidinyl)-5-azaindole;
1-(2,6-Dimethoxybenzoyl)-3-(1,2,3,5,8,8a-hexahydro-7-indolizinyl)-5-azaindole;
1-(2-Chlorobenzoyl)-3-(1,2,3,5,8,8a-hexahydro-7-indolizinyl)-5-azaindole;
1-(4-Chlorobenzenesulfonyl)-3-(1,2,3,5,8,8a-hexahydro-7-indolizinyl-5-azaindole;

1-(4-Fluorobenzenesulfonyl)-3-(1,2,3,5,8,8a-hexahydro-7-indolizinyl)-5-azaindole;
1-Benzoyl-3-(1,2,3,5,8,8a-hexahydro-7-indolizinyl)-5-azaindole;
1-(1-Naphthalenesulfonyl)-3-(octahydro-8-quinolizinyl)-5-azaindole;
3-(1,2,3,5,8,8a-Hexahydro-7-indolizinyl)-1-(4-methylbenzenesulfonyl)-5-azaindole;
3-(1,2,3,5,8,8a-Hexahydro-7-indolizinyl)-1H-5-azaindole;
3-(1,2,3,5,8,8a-Hexahydro-7-indolizinyl)-1-(1-naphthalenesulfonyl)-5-azaindole;
3-(1,2,3,5,8,8a-Hexahydro-7-indolizinyl)-1-benzenesulfonyl-5-azaindole;
3-(1,2,3,5,8,8a-Hexahydro-7-indolizinyl)-1-(2-naphthalenesulfonyl)-5-azaindole;
3-(1,2,4,6,7,9a-Hexahydro-2H-quinolizine-2-yl)-5-azaindole;
3-(1-Methyl-1,2,3,6-tetrahydro-4-pyridinyl)-1-benzenesulfonyl-5-azaindole;
3-(1-Methyl-1,2,3,6-tetrahydro-4-pyridinyl)-5-azaindole;
3-(1-Methyl-4-piperidinyl)-5-azaindole;
3-(1-Methyl-4-piperidinyl)-1-benzenesulfonyl-5-azaindole;
3-(Octahydro-7-indolizinyl)-1H-5-azaindole;
3-(Octahydro-7-indolizinyl)-1-(1-naphthalenesulfonyl)-5-azaindole;
3-(Octahydro-7-indolizinyl)-1-(1-naphthalenesulfonyl)-5-azaindole;
3-(Octahydro-7-indolizinyl)-1-benzenesulfonyl-5-azaindole;
3-(Octahydro-7-indolizinyl)-1-benzenesulfonyl-5-azaindole;
3-(Octahydro-7-indolizinyl)-2,5-dichlorobenzenesulfonyl-5-azaindole;
3-(Octahydro-7-indolizinyl)-2,5-dichlorobenzenesulfonyl-5-azaindole;
3-(Octahydro-7-indolizinyl)-2,5-dichlorobenzenesulfonyl-5-azaindole;
3-(Octahydro-7-indolizinyl)-1-(2-naphthalenesulfonyl)-5-azaindole;
3-(Octahydro-7-indolizinyl)-1-(2-naphthalenesulfonyl)-5-azaindole;
3-(Octahydro-quinolizine)-1H-5-azaindole;
3-(1,2,3,5,8,8a-Hexahydro-7-indolizinyl)-1H-6-azaindole;
3-(1,2,3,5,8,8a-Hexahydro-7-indolizinyl)-1-(1-naphthalenesulfonyl)-6-azaindole;
3-(Octahydro-7-indolizinyl)-1H-6-azaindole;
3-(Octahydro-7-indolizinyl)-1-(1-naphthalenesulfonyl)-6-azaindole;
3-(Octahydro-7-indolizinyl)-1-(1-naphthalenesulfonyl)-6-azaindole;
1-(2,6-Dichlorobenzoyl)-3-(1,2,3,5,8,8a-hexahydro-7-indolizinyl)-7-azaindole;
1-(2,6-Dimethoxybenzoyl)-3-(1,2,3,5,8,8a-hexahydro-7-indolizinyl)-7-azaindole;
1-(4-Chlorobenzenesulfonyl)-3-(1,2,3,5,8,8a-hexahydro-7-indolizinyl)-7-azaindole;
1-(4-Fluorobenzoyl)-3-(1-methyl-1,2,3,6-tetrahydro-4-pyridinyl)-7-azaindole;
1-(4-Fluorobenzenesulfonyl)-3-(1,2,3,5,8,8a-hexahydro-7-indolizinyl)-7-azaindole;
1-(4-Fluorobenzenesulfonyl)-3-(1-methyl-1,2,3,6-tetrahydro-4-pyridinyl)-7-azaindole;
1-(4-Methoxybenzoyl)-3-(1-methyl-1,2,3,6-tetrahydro-4-pyridinyl)-7-azaindole;
1-(4-Methoxybenzenesulfonyl)-3-(1-methyl-1,2,3,6-tetrahydro-4-pyridinyl)-7-azaindole;
1-Benzoyl-3-(1,2,3,5,8,8a-hexahydro-7-indolizinyl)-7-azaindole;
1-Benzoyl-3-(1-methyl-1,2,3,6-tetrahydro-4-pyridinyl)-7-azaindole;
3-(1,2,3,5,8,8a-Hexahydro-7-indolizinyl)-1-(4-methylbenzenesulfonyl)-7-azaindole;
3-(1,2,3,5,8,8a-Hexahydro-7-indolizinyl)-1H-7-azaindole;
3-(1,2,3,5,8,8a-Hexahydro-7-indolizinyl)-1-(1-naphthalenesulfonyl)-7-azaindole;
3-(1,2,3,5,8,8a-Hexahydro-7-indolizinyl)-1-benzenesulfonyl-7-azaindole;
3-(1,2,3,5,8,8a-Hexahydro-7-indolizinyl)-1-(2-naphthalenesulfonyl)-7-azaindole;
3-(1-Methyl-1,2,3,6-tetrahydro-4-pyridinyl)-1-benzenesulfonyl-7-azaindole;
3-(Octahydro-7-indolizinyl)-1H-7-azaindole;
3-(Octahydro-7-indolizinyl)-1-(1-naphthalenesulfonyl)-7-azaindole;
3-(Octahydro-7-indolizinyl)-1-(1-naphthalenesulfonyl)-7-azaindole;
3-(Octahydro-7-indolizinyl)-1-benzenesulfonyl-7-azaindole;
3-(Octahydro-7-indolizinyl)-1-(2-naphthalenesulfonyl)-7-azaindole; and
3-(Octahydro-7-indolizinyl)-1-(2-naphthalenesulfonyl)-7-azaindole.

In preferred embodiments of the invention, the compounds of Formula I include:
1-(2,6-Dichlorobenzoyl)-3-(1,2,3,5,8,8a-hexahydro-7-indolizinyl)-1H-5-azaindole;
1-(2,6-Dichlorobenzoyl)-3-(1,2,3,5,8,8a-hexahydro-7-indolizinyl)-1H-7-azaindole;
1-(2,6-Dichlorobenzoyl)-3-(1-methyl-1,2,3,6-tetrahydro-4-pyridinyl)-1H-5-azaindole;
1-(2,6-Dichlorobenzoyl)-3-(1-methyl-4-piperidinyl)-1H-5-azaindole;
1-(2,6-Dimethoxybenzoyl)-3-(1,2,3,5,8,8a-hexahydro-7-indolizinyl)-1H-5-azaindole;
1-(2,6-Dimethoxybenzoyl)-3-(1,2,3,5,8,8a-hexahydro-7-indolizinyl)-1H-7-azaindole;
1-(2-Chlorobenzoyl)-3-(1,2,3,5,8,8a-hexahydro-7-indolizinyl)-1H-5-azaindole;
1-(4-Fluorobenzoyl)-3-(1-methyl-1,2,3,6-tetrahydro-4-pyridinyl)-1H-7-azaindole;
1-(4-Methoxybenzoyl)-3-(1-methyl-1,2,3,6-tetrahydro-4-pyridinyl)-1H-7-azaindole;
1-Benzoyl-3-(1,2,3,5,8,8a-hexahydro-7-indolizinyl)-1H-5-azaindole;
1-Benzoyl-3-(1,2,3,5,8,8a-hexahydro-7-indolizinyl)-1H-7-azaindole; and
1-Benzoyl-3-(1-methyl-1,2,3,6-tetrahydro-4-pyridinyl)-1H-7-azaindole.

In more preferred embodiments of the invention, the compounds of Formula I include:
1-(4-Chlorobenzenesulfonyl)-3-(1,2,3,5,8,8a-hexahydro-7-indolizinyl-1H-7-azaindole;
1-(4-Chlorobenzenesulfonyl)-3-(1,2,3,5,8,8a-hexahydro-7-indolizinyl-1H-5-azaindole;
1-(4-Fluorobenzenesulfonyl)-3-(1,2,3,5,8,8a-hexahydro-7-indolizinyl)-1H-7-azaindole;
1-(4-Fluorobenzenesulfonyl)-3-(1,2,3,5,8,8a-hexahydro-7-indolizinyl)-1H-5-azaindole;
1-(4-Fluorobenzenesulfonyl)-3-(1-methyl-1,2,3,6-tetrahydro-4-pyridinyl)-1H-7-azaindole;
1-(4-Methoxybenzenesulfonyl)-3-(1-methyl-1,2,3,6-tetrahydro-4-pyridinyl)-1H-7-azaindole;

3-(1,2,3,5,8,8a-Hexahydro-7-indolizinyl)-1-(4-methylbenzenesulfonyl)-1H-7-azaindole;
3-(1,2,3,5,8,8a-Hexahydro-7-indolizinyl)-1-(4-methylbenzenesulfonyl)-1H-5-azaindole;
3-(1,2,3,5,8,8a-Hexahydro-7-indolizinyl)-1-benzenesulfonyl-1H-5-azaindole;
3-(1,2,3,5,8,8a-Hexahydro-7-indolizinyl)-1-benzenesulfonyl-1H-7-azaindole;
3-(1-Methyl-1,2,3,6-tetrahydro-4-pyridinyl)-1-benzenesulfonyl-1H-5-azaindole;
3-(1-Methyl-1,2,3,6-tetrahydro-4-pyridinyl)-1-benzenesulfonyl-1H-7-azaindole;
3-(1-Methyl-4-piperidinyl)-1-benzenesulfonyl-1H-5-azaindole;
3-(Octahydro-7-indolizinyl)-1-benzenesulfonyl-1H-5-azaindole;
3-(Octahydro-7-indolizinyl)-1-benzenesulfonyl-1H-7-azaindole; and
3-(Octahydro-7-indolizinyl)-2,5-dichlorobenzenesulfonyl-1H-5-azaindole.

In the most preferred embodiments of the invention, the compounds of Formula I include:
1-(1-Naphthalenesulfonyl)-3-(octahydro-4-quinolizinyl)-1H-5-azaindole;
3-(1,2,3,5,8,8a-Hexahydro-7-indolizinyl)-1-(1-naphthalenesulfonyl)-1H-6-azaindole;
3-(1,2,3,5,8,8a-Hexahydro-7-indolizinyl)-1-(1-naphthalenesulfonyl)-1H-7-azaindole;
3-(1,2,3,5,8,8a-Hexahydro-7-indolizinyl)-1-(1-naphthalenesulfonyl)-1H-5-azaindole;
3-(1,2,3,5,8,8a-Hexahydro-7-indolizinyl)-1-(2-naphthalenesulfonyl)-1H-5-azaindole;
3-(1,2,3,5,8,8a-Hexahydro-7-indolizinyl)-1-(2-naphthalenesulfonyl)-1H-7-azaindole;
3-(Octahydro-7-indolizinyl)-1-(1-naphthalenesulfonyl)-1H-4-azaindole;
3-(Octahydro-7-indolizinyl)-1-(1-naphthalenesulfonyl)-1H-5-azaindole;
3-(Octahydro-7-indolizinyl)-1-(1-naphthalenesulfonyl)-1H-6-azaindole;
3-(Octahydro-7-indolizinyl)-1-(1-naphthalenesulfonyl)-1H-7-azaindole;
3-(Octahydro-7-indolizinyl)-1-(2-naphthalenesulfonyl)-1H-4-azaindole;
3-(Octahydro-7-indolizinyl)-1-(2-naphthalenesulfonyl)-1H-5-azaindole; and
3-(Octahydro-7-indolizinyl)-1-(2-naphthalenesulfonyl)-1H-7-azaindole.

Compounds of Formula I may have at least one asymmetric centre. Where the compounds according to the invention have one asymmetric centre they may exist as enantiomers. Where the compounds according to the invention possess two or more asymmetric centres, they may additionally exist as diastereomers. It is to be understood that all such isomers and mixtures thereof in any proportion are encompassed within the scope of the present invention.

The conversion of a given compound salt to a desired compound salt is achieved by applying standard techniques, in which an aqueous solution of the given salt is treated with either a solution of a base e.g. sodium carbonate or potassium hydroxide, or an acid, e.g. HCl (caution when Z═N), to liberate the neutral compound which is then extracted into an appropriate solvent, such as ether. The neutral compound is then separated from the aqueous portion, dried, and treated with the requisite acid or base to give the desired salt.

Also included within the scope of the invention are solvates of the invention. The formation of the solvate will vary depending on the compound and solvent used. In general, solvates are formed by dissolving the compound in the appropriate solvent and isolating the solvate by cooling or using an antisolvent. The solvate is typically dried or azeotroped under ambient conditions.

Prodrugs of compounds of Formula I may be conventional esters with available hydroxyl (or thiol) or carboxyl groups. For example, if a substituent of a compound of Formula I is, or contains, a hydroxyl group, it may be acylated using an activated acid in the presence of a base and, optionally, in inert solvent (e.g. an acid chloride in pyridine). Some common esters which have been utilized as prodrugs are phenyl esters, aliphatic ($C_1$-$C_{24}$) esters, acyloxymethyl esters, carbamates and amino acid esters.

In accordance with other aspects of the invention, the compounds of the present invention can be prepared by processes analogous to those established in the art.

For example, as shown in Scheme 1, compounds of Formula I (wherein $R_1$ is $SO_2Ar$, $C(O)Ar$ or $CH_2 Ar$) may be prepared by first treating compounds of Formula IV with a suitable base, followed by the addition of reagent $R_1$—Y, where Y is a suitable leaving group such as halo, arylsulfonyloxy or alkylsulfonyloxy. Preferably Y is chloro. Suitable bases include sodium hydride, lithium diisopropylamide, n-butyllithium or sodium bis(trimethylsilyl)amide, the reaction being carried out in an inert solvent such as dimethyl formamide, tetrahydrofuran or hexanes at a temperature in the range of −100 to 30° C. Alternatively an organic amine in the presence of 4-dimethylaminopyridine (DMAP) can be used, the reaction being carried out in an inert solvent such as methylene chloride or chloroform, at a temperature in the range of 0-60° C. Preferred conditions are sodium bis(trimethylsilyl)amide in tetrahydrofuran at temperatures in the range of 0° C. to room temperature, or triethylamine and DMAP in methylene chloride at room temperature. Reagents $R_1$—Y are commercially available or can be prepared using standard methods known to those skilled in the art. The preparation of compounds of Formula IV is described below.

Scheme 1

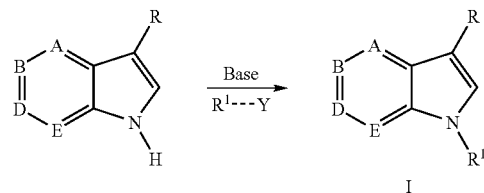

Compounds of Formula I wherein $R_1$ is Ar may be prepared as shown in Scheme 2, below. Treatment of IV with an aryl halide (wherein Ar is as defined in Formula I) under standard Ullmann arylation conditions, for example in the presence of a base such as potassium carbonate and a catalyst such as copper, copper (I) iodide or copper (I) bromide or mixtures thereof, in an inert solvent such as N-methylpyrrolidinone (NMP), dimethylformamide (DMF), hexamethylphosphoramide (HMPA) or dimethylsulfoxide (DMSO) at temperatures in the range of 150-200° C. Preferred conditions are copper (I) bromide and copper in NMP at temperatures in the range of 160-170° C.

Scheme 2

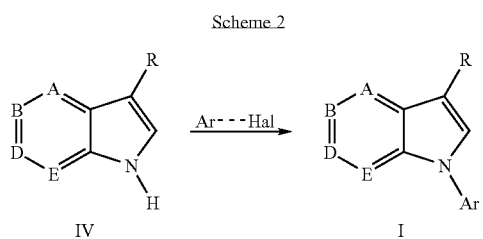

Compounds of Formula IV wherein R is a group of Formula III may be prepared by a number of routes. For example, as shown in Scheme 3, below, compound A (where PG is a suitable protecting group), may be condensed with reagent B, under acidic conditions, to provide regioisomeric products C and C'. The reaction is carried out in a suitable solvent, at temperatures in the range of 25-100° C., preferably within the range 60-90° C. Suitable conditions include, for example, trifluoroacetic acid in acetic acid at a temperature in the range of 50-120° C., preferably at around 110° C.

conditions to give product IV. Preferred conditions for this deprotection are sodium hydroxide in methanol, at temperatures in the range of −20-100° C., suitably −10-8° C. PG may also be, for example, a tosyl group, which can be removed under acidic conditions (for example HBr in acetic acid). It should be understood that the criteria for selection of a suitable protecting group would be known to a person skilled in the art as described in *Protective Groups in Organic Chemistry*, ed. McOmie, J. F. W. Plenum Press, 1973; and Greene, T. W. & Wuts, P. G. M., *Protective Groups in Organic Synthesis*, John Wiley & Sons, 1991.

It should be noted that, in the series of reactions described above, the presence of the protecting group PG may not always be necessary, depending upon the exact nature of any substituents present. In such cases compounds of Formula IV could be obtained directly from compounds of Formula A where PG is replaced with H. In this case the reaction may proceed under either acidic or basic conditions. When the reaction is carried out in basic conditions, typically regioisomer C is the sole product isolated. Suitable basic conditions include the use of organic amines such as pyrrolidine or

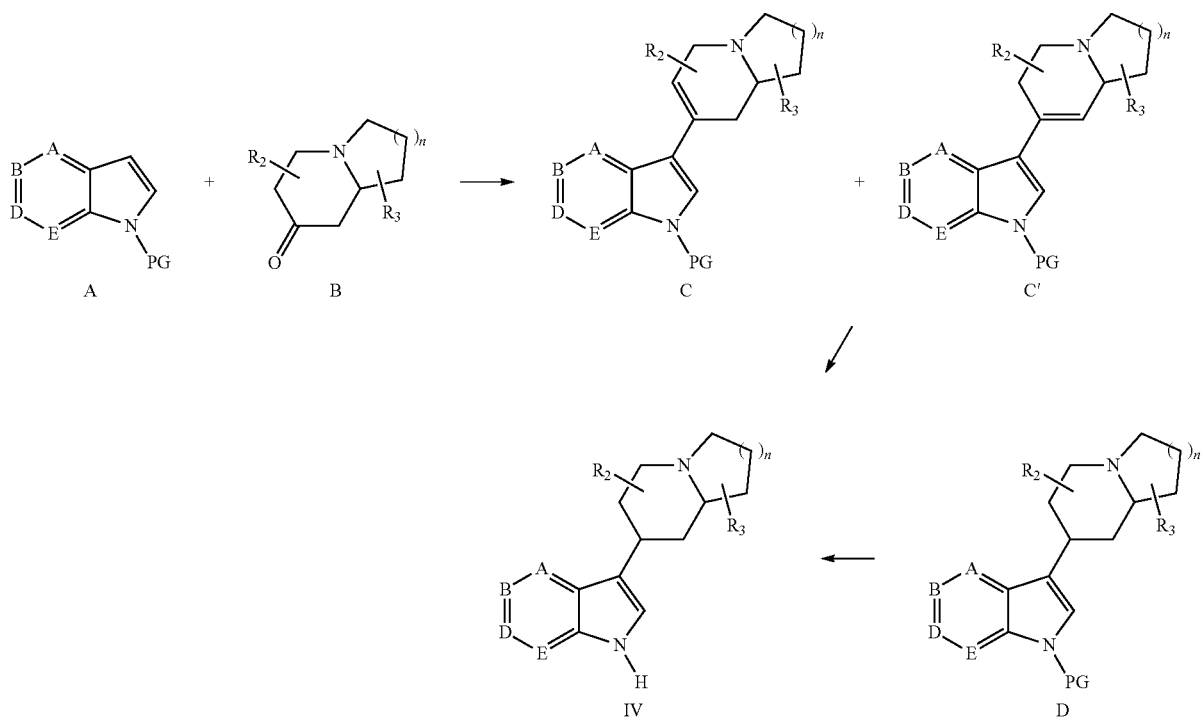

Under these reaction conditions both regioisomneric alkenes C and C' may be isolated, the ratio of which will vary according to the reaction conditions and the identity and position of $R_2$. When $R_2$ is H, this ratio is typically 1:1.

Compounds C and C' may be reduced under standard conditions (using, for example, metal hydrides) to provide compounds D. Preferred is reduction by hydrogenation, using a suitable catalyst such as palladium or platinum on carbon in methanol or ethanol at room temperature. Compounds D can exist in isomeric forms which may be separable, for example by column chromatography, to yield so-called less polar and more polar isomers.

Deprotection of compound D under standard conditions yields compound IV. For example, when PG is an acetate group, this can be hydrolyzed under either basic or acidic piperidine in solvents such as methanol, ethanol and the like. Preferred basic conditions are pyrrolidine in ethanol at a refluxing temperature.

Compounds of Formula H (i.e. compounds of Formula IV in which R is a group of Formula III, Z is a nitrogen atom and ---are single bonds) may be prepared as shown in Scheme 4, below. Compounds E or F, wherein PG is a suitable protecting group such as acetate or tosyl, may be reacted with bicyclic piperazine G in the presence of a catalytic amount of an acid, such as p-toluenesulfonic acid or camphorsulfonic acid, the reaction being carried out in an inert solvent such as toluene or benzene, at temperatures in the range of 25-120° C., to provide compounds H. Preferred conditions are p-toluenesulfonic acid in toluene at a refluxing temperature. Compound H can be deprotected, as previously described, to provide compound J.

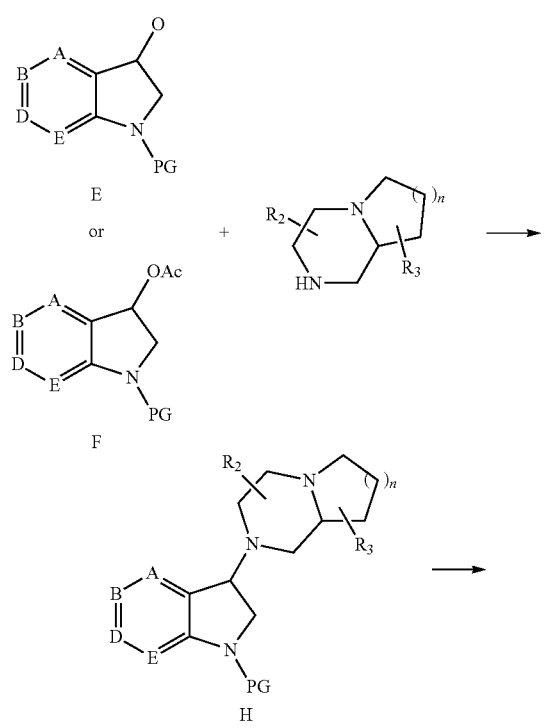

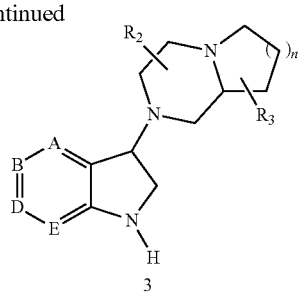

Bicyclic piperidinones B and piperazines G are either commercially available or can be prepared using procedures known in the art. For example, bicyclic piperidinones of Formula B may be prepared according to procedures described in King, F. D., J. Chem. Soc. Perkin Trans. I, 1986: 447-453 and bicyclic piperazines of Formula G may be prepared according to procedures described in Power, P. et al., U.S. Pat. No. 5,576,314; Saleh, M. A. et al. J. Org. Chem. 58, 1993:690-695; Urban, F. J. Heterocyclic Chem. 32, 1995: 857-861; Bright, G. et al. WO 90/08148; de Costa, B. R. et al. J. Med. Chem. 36, 1993:2311-2320; and Botre, C. et al. J. Med. Chem. 29, 1986:1814-1820.

Compounds of Formula I in which R is a group of Formula II may be prepared in an analogous fashion, as shown in Scheme 5, below. Condensation of azaindole K with an appropriately-substituted piperidone gives compound L, which may be reduced to give compound M (or, alternatively, derivatized to yield compound O). Again, M can exist in isomeric forms, which may be separable by chromatography. Compound M can be derivatized as previously described to give the desired product N.

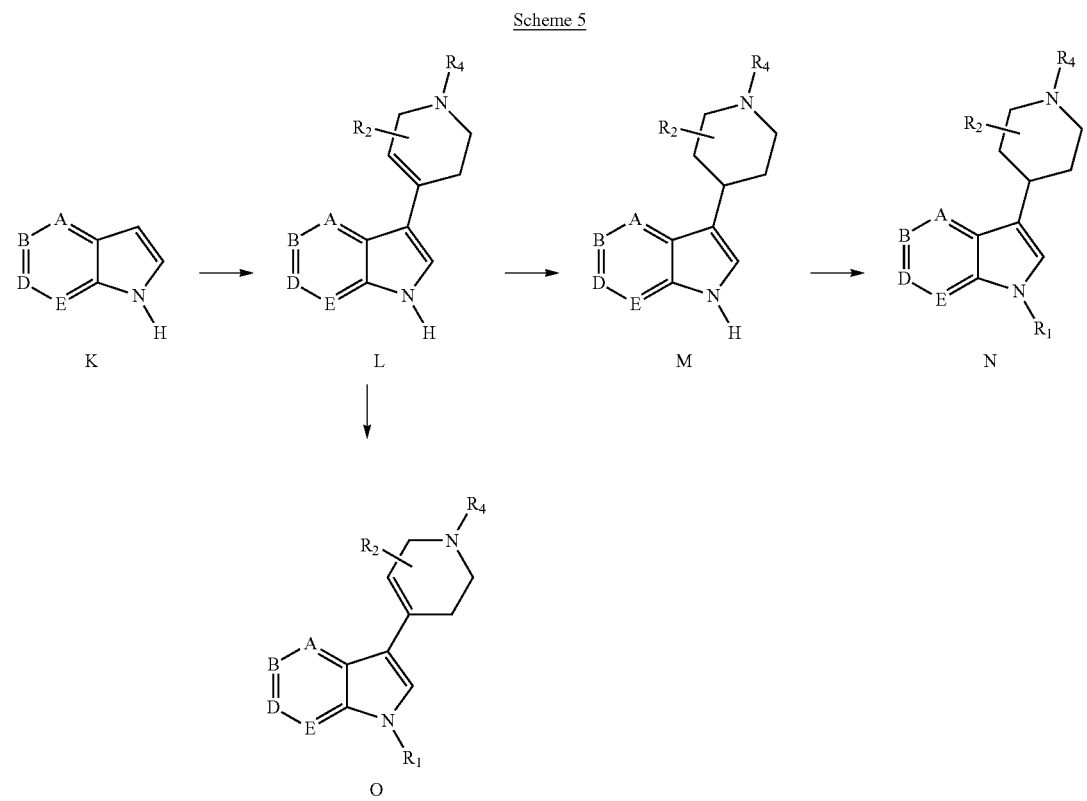

The starting azaindoles in the above synthetic schemes may be purchased (in the case of 7-azaindole) or prepared by techniques well known in the art. For example, 4-Azaindoles may be prepared according to the method of Sakamoto et al., Chem. Pharm. Bull., 34, 1986, p 2362-2368. 5-Azaindoles may be prepared according to the method of Sakamoto et al., Heterocycles, 34, 1992, p 2379-2384; or, alternatively, according to the method of Hands, et al., Synthesis, 1996, p 877-882. This latter method can also be used to prepare 6- and 7-azaindoles.

It should be noted that one skilled in the art would realize that the sequence of reactions described above for the preparation of compounds of Formula I can be varied. For example, the $R_1$ group may be incorporated into the molecule before the addition of the group at the indole 3-position.

In some cases, the chemistries outlined above may have to be modified, for instance by use of protecting groups, to prevent side reactions due to reactive groups, such as reactive groups attached as substituents. This may be achieved be means of conventional protecting groups, as described in *Protective Groups in Organic Chemistry*, ed. McOmie, J. F. W. Plenum Press, 1973; and Greene, T. W. & Wuts, P. G. M., *Protective Groups in Organic Synthesis*, John Wiley &

In another of its aspects, the present invention provides compounds of Formula IV. Whilst certain compounds of Formula IV also bind to the 5-$HT_6$ receptor such compounds are more generally useful as intermediates in the preparation of compounds of Formula I.

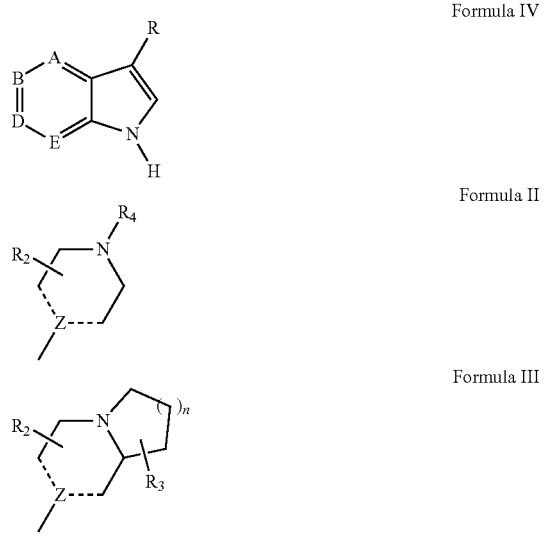

Formula IV

Formula II

Formula III and a salt, solvate or hydrate thereof, wherein

R represents a group of Formula II or Formula III;

one of A, B D or E is a N atom, the remainder being CH groups;

$R_2$, $R_3$ and $R_4$ are independently selected from the group consisting of H and alkyl;

----represents a single or double bond, with the proviso that there is only one double bond in the ring at a time;

n is an integer of from 1-3;

Z is selected from the group consisting of C, CH and N, provided that when ----is a double bond, Z is C and when ----is a single bond, Z is selected from CH and N.

Compounds of Formula IV can be converted into compounds of Formula I as shown above.

Certain compounds of Formula I also bind to the 5-$HT_7$ receptor, and a further object of the invention provides compounds (for example 5-azaindoles wherein R is a saturated group of Formula III) having mixed 5-$HT_6$ and 5-$HT_7$ activity.

In a further embodiment of the invention, compounds of Formula I can be used to distinguish 5-$HT_6$ receptors from other receptor subtypes, for example glutamate or opioid receptors, within a population of receptors, and in particular to distinguish between the 5-$HT_6$ and other 5-HT receptor subtypes. The latter can be achieved by incubating preparations of the 5-$HT_6$ receptor and one of the other 5-HT receptor subtypes (for example 5-$HT_{2A}$) with a 5-$HT_6$-selective compound of the invention and then incubating the resulting preparation with a radiolabeled serotonin receptor ligand, for example [$^3$H]-serotonin. The 5-$HT_6$ receptors are then distinguished by determining the difference in membrane-bound activity, with the 5-$HT_6$ receptor exhibiting lesser radioactivity, i.e., lesser [$^3$H]-serotonin binding, than the other 5-HT receptor subtype.

In another embodiment of the invention, a compound of Formula I is provided in labeled form, such as radiolabeled form, e.g. labeled by incorporation within its structure $^3$H or $^{14}$C or by conjugation to $^{125}$I. In another aspect of the invention, the compounds in labeled form can be used to identify 5-$HT_6$ receptor ligands by techniques common in the art. This can be achieved by incubating the receptor or tissue in the presence of a ligand candidate and then incubating the resulting preparation with an equimolar amount of radiolabeled compound of the invention such as. 5-$HT_6$ receptor ligands are thus revealed as those that are not significantly displaced by the radiolabeled compound of the present invention. Alternatively, 5-$HT_6$ receptor ligand candidates may be identified by first incubating a radiolabeled form of a compound of the invention then incubating the resulting preparation in the presence of the candidate ligand. A more potent 5-$HT_6$ receptor ligand will, at equimolar concentration, displace the radiolabeled compound of the invention.

A radiolabelled compound of Formula I may be prepared using standard methods known in the art. For example a compound of Formula I wherein Ar is substituted with a radioactive iodo group may be prepared from the corresponding trialkyltin (suitably trimethyltin) derivative using standard iodination conditions, such as [$^{125}$I] sodium iodide in the presence of chloramine-T in a suitable solvent, such as dimethylformamide. The trialkyltin compound may be prepared from the corresponding non-radioactive halo, suitably iodo, compound using standard palladium-catalyzed stannylation conditions, for example hexamethylditin in the presence of tetrakis(triphenylphosphine) palladium (0) in an inert solvent, such as dioxane, and at elevated temperatures, suitably 50-100° C. Alternatively, tritium may be incorporated into a compound of Formula I using standard techniques, for example by hydrogenation of a suitable precursor to a compound of Formula I using tritium gas and a catalyst.

Compounds of Formula I are useful as pharmaceuticals for the treatment of various conditions in which the use of a 5-$HT_6$ antagonist is indicated, such as psychosis, schizophrenia, manic depression, depression, neurological disturbances, memory disturbances, Parkinsonism, amylotrophic lateral sclerosis, Alzheimer's disease and Huntington's disease. In another of its aspects, the present invention provides pharmaceutical compositions useful to treat 5-$HT_6$-related medical conditions, in which a compound of Formula I is present in an amount effective to antagonize 5-$HT_6$ receptor stimulation, together with a pharmaceutically acceptable carrier. In a related aspect, the invention provides a method for treating medical conditions for which a 5-HT$_6$ receptor antagonist is indicated, which comprises the step of administering to the patient an amount of a compound of Formula I effective to antagonize 5-HT$_6$ receptor stimulation, and a pharmaceutically acceptable carrier thereof.

For use in medicine, the compounds of the present invention can be administered in a standard pharmaceutical composition. The present invention therefore provides, in a further aspect, pharmaceutical compositions comprising a pharmaceutically acceptable carrier and a Formula I compound or a pharmaceutically acceptable salt, solvate or hydrate thereof, in an amount effective to treat the target indication.

The compounds of the present invention may be administered by any convenient route, for example by oral, parenteral, buccal, sublingual, nasal, rectal, patch, pump or transdermal administration and the pharmaceutical compositions formulated accordingly.

Compounds of Formula I and their pharmaceutically acceptable salts which are active when given orally can be formulated as liquids, for example syrups, suspensions or emulsions, or as solid forms such as tablets, capsules and lozenges. A liquid formulation will generally consist of a suspension or solution of the compound or pharmaceutically acceptable salt in a suitable pharmaceutical liquid carrier for example, ethanol, glycerine, non-aqueous solvent, for example polyethylene glycol, oils, or water with a suspending agent, preservative, flavouring or colouring agent. A composition in the form of a tablet can be prepared using any suitable pharmaceutical carrier routinely used for preparing solid formulations. Examples of such carriers include magnesium stearate, starch, lactose, sucrose and cellulose. A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier, for example aqueous gums, celluloses, silicates or oils and the dispersion or suspension filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilized and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

Preferably, the composition is in unit dose form such as a tablet, capsule or ampoule. Suitable unit dosages, i.e. therapeutically effective amounts, can be determined during clinical trials designed appropriately for each of the conditions for which administration of a chosen compound is indicated and will of course vary depending on the desired clinical endpoint. Each dosage unit for oral administration may contain from 0.01 to 500 mg/kg (and for parenteral administration may contain from 0.1 to 50 mg) of a compound of Formula I, or a pharmaceutically acceptable salt thereof calculated as the free base, and will be administered in a frequency appropriate for initial and maintenance treatments. For laboratory use, the present compounds can be stored in packaged form for reconstitution and use.

EXPERIMENTAL EXAMPLES

Example 1

3-(1,2,3,5,8,8a-Hexahydro-7-indolizinyl)-1H-5-azaindole

A mixture of 5-azaindole (0.5 g, 4.23 mmol), 1,2,3,5,6,8,8a-heptahydrohydro-7-oxo-indolizine (589 mg, 4.23 mmol) and pyrrolidine (3.0 g, 42.3 mmol) in ethanol (4 mL) were heated to reflux for 6 hrs. The reaction mixture was cooled, filtered, and the collected solid washed with ether to give 3-(1,2,3,5,8,8a-hexahydro-7-indolizinyl)-1H-5-Azaindole (0.521 g, 51.6%).

In a similar fashion, the following compounds were prepared:

3-(1,2,4,6,7,9a-Hexahydro-2H-quinolizine-2-yl)-5-azaindole (0.167 g, 50.6%); from 5-azaindole (154 mg, 1.3 mmol), octahydro-quinolizine-2-one (200 mg, 1.3 mmol) and pyrrolidine (0.7 mL) in ethanol (1.2 mL), heating at reflux overnight.

3-(1-Methyl-1,2,3,6-tetrahydro-4-pyridinyl)-5-azaindole (1.754 g, 49%); from 5-azaindole (2.0 g, 16.9 mmol); N-methyl-4-piperidone (1.92 g, 16.9 mmol) and pyrrolidine (12.04 g, 169 mmol) in ethanol (20 mL).

3-(1,2,3,5,8,8a-Hexahydro-7-indolizinyl)-1H-4-azaindole (792 mg, 39%); from 4-azaindole (1.0 g, 8.46 mmol), 1,2,3,5,6,8,8a-heptahydrohydro-7-oxo-indolizine (1.77 g, 12.7 mmol) and pyrrolidine (3.5 g, 42.3 mmol) in ethanol (8 mL), heating at reflux for 3 hrs.

3-(1,2,3,5,8,8a-Hexahydro-7-indolizinyl)-1H-6-azaindole (273 mg, 53.9%); from 6-azaindole (250 mg, 2.1 mmol), 1,2,3,5,6,8,8a-heptahydrohydro-7-oxo-indolizine (324 mg, 2.3 mmol) and pyrrolidine (1.2 g, 16.9 mmol) in ethanol (2 mL) heating at reflux for 6 hrs.

3-(1,2,3,5,8,8a-Hexahydro-7-indolizinyl)-1H-7-azaindole (396 mg, 39.3%); from 7-azaindole (500 mg, 4.2 mmol), 1,2,3,5,6,8,8a-heptahydrohydro-7-oxo-indolizine (589 mg, 4.2 mmol) and pyrrolidine (3.0 g, 42 mmol) in ethanol (4 mL) heating at reflux for 5 hrs.

Example 2

1-(2-Chlorobenzoyl)-3-(1,2,3,5,8,8a-hexahydro-7-indolizinyl)-5-azaindole

To a THF (1 mL) solution of 3-(1,2,3,5,8,8a-Hexahydro-7-indolizinyl)-1H-5-azaindole (10 mg, 0.0418 mmol) at RT, 1M NaN(TMS)2 (100 µL, 0.1 mmol) was added and the mixture stirred for 10 mins. 2-chlorobenzoyl chloride (13 μL, 0.103 mmol) was added and the reaction mixture stirred overnight. After dilution with dichloromethane, purification by column chromatography with 2% methanol (2M/NH$_3$) in dichloromethane gave 1-(2-chlorobenzoyl)-3-(1,2,3,5,8,8a-hexahydro-7-indolizinyl)-5-azaindole (8.9 mg, 56.4%).

In a similar fashion, the following compounds were prepared:

1-(2,6-Dichlorobenzoyl)-3-(1,2,3,5,8,8a-hexahydro-7-indolizinyl)-5-azaindole (4.2 mg, 24.4%); from 3-(1,2,3,5,8,8a-hexahydro-7-indolizinyl)-1H-5-Azaindole (10 mg, 0.0418 mmol), 2-chlorobenzoyl chloride (13 μL, 0.0907 mmol) and 1M NaN(TMS)2 (100 μL, 0.10 mmol) in THF (1 mL) at RT.

1-(2,6-Dimethoxybenzoyl)-3-(1,2,3,5,8,8a-hexahydro-7-indolizinyl)-5-azaindole (9.4 mg, 55.8%); from 3-(1,2,3,5,8,8a-hexahydro-7-indolizinyl)-1H-5-Azainddle (10 mg, 0.0418 mmol), 2,6-dimethoxybenzoyl chloride (20 mg, 0.0997 mmol) and 1M NaN(TMS)2 (100 μL, 0.10 mmol) in THF (1 mL) at RT.

1-Benzoyl-3-(1,2,3,5,8,8a-hexahydro-7-indolizinyl)-5-azaindole (5.8 mg, 41.5%); from 3-(1,2,3,5,8,8a-hexahydro-7-indolizinyl)-1H-5-Azaindole (10 mg, 0.0418 mmol), benzoyl chloride (13 μL, 0.12 mmol) and 1M NaN(TMS)2 (100 μL, 0.10 mmol) in THF (1 mL) at RT.

3-(1,2,3,5,8,8a-Hexahydro-7-indolizinyl)-1-benzenesulfonyl-5-azaindole (4.8 mg, 30.3%); from 3-(1,2,3,5,8,8a-hexahydro-7-indolizinyl)-1H-5-Azaindole (10 mg, 0.0418 mmol), benzenesulfonyl chloride (20 mg, 0.113 mmol) and 1M NaN(TMS)2 (100 μL, 0.10 mmol) in THF (0.5 mL) at RT.

1-(4-Fluorobenzenesulfonyl)-3-(1,2,3,5,8,8a-hexahydro-7-indolizinyl)-5-azaindole (5.9 mg, 35.5%); from 3-(1,2,3,5,8,8a-hexahydro-7-indolizinyl)-1H-5-Azaindole (10 mg, 0.0418 mmol), 4-fluorobenzenesulfonyl chloride (20 mg, 0.103 mmol) and 1M NaN(TMS)2 (100 μL, 0.10 mmol) in THF (0.5 mL) at RT.

1-(4-Chlorobenzenesulfonyl)-3-(1,2,3,5,8,8a-hexahydro-7-indolizinyl-5-azaindole (6.3 mg, 36.4%); from 3-(1,2,3,5,8,8a-hexahydro-7-indolizinyl1H-5-Azaindole (10 mg, 0.0418 mmol), 4-chlorobenzenesulfonyl chloride (20 mg, 0.095 mmol) and 1M NaN(TMS)2 (100 μL, 0.10 mmol) in THF (0.5 mL) at RT.

3-(1,2,3,5,8,8a-Hexahydro-7-indolizinyl)-1-(4-methylbenzenesulfonyl)-5-azaindole (8.9 mg, 54.1%); from 3-(1,2,3,5,8,8a-hexahydro-7-indolizinyl)-1H-5-Azaindole (10 mg, 0.0418 mmol), 4-methylbenzenesulfonyl chloride (20 mg, 0.105 mmol) and 1M NaN(TMS)2 (100 μL, 0.10 mmol) in THF (0.5 mL) at RT.

3-(1,2,3,5,8,8a-Hexahydro-7-indolizinyl)-1-(1-naphthalenesulfonyl)-5-azaindole (8.9 mg, 49.6%); from 3-(1,2,3,5,8,8a-hexahydro-7-indolizinyl)-1H-5-Azaindole (10 mg, 0.0418 mmol), 1-naphthalenesulfonyl chloride (20 mg, 0.088 mmol) and 1M NaN(TMS)2 (100 μL, 0.10 mmol) in THF (0.5 mL) at RT.

3-(1,2,3,5,8,8a-Hexahydro-7-indolizinyl)-1-(2-naphthalenesulfonyl)-5-azaindole (8.3 mg, 46.2%); 3-(1,2,3,5,8,8a-hexahydro-7-indolizinyl)-1H-5-Azaindole (10 mg, 0.0418 mmol), 2-naphthalenesulfonyl chloride (20 mg, 0.088 mmol) and 1M NaN(TMS)2 (100 μL, 0.10 mmol) in THF (0.5 mL) at RT.

3-(Octahydro-7-indolizinyl)-1-benzenesufonyl-5-azaindole (11.9 mg, 75.3%); from 3-(octahydro-7-indolizinyl)-1-H-5-azaindole (10 mg, 0.0415 mmol), benzene-sulfonyl chloride (12 μL, 0.094 mmol) and 1M NaN(TMS)2 (100 μL, 0.10 mmol) in THF (0.5 mL) at RT.

3-(Octahydro-7-indolizinyl)-1-(1-naphthalenesulfonyl)-5-azaindole (15.4 mg, 86%); from 3-(octahydro-7-indolizinyl)-1-H-5-azaindole (10 mg, 0.0415 mmol), 1-naphthalenesulfonyl chloride (15 mg, 0.072 mmol) and 1M NaN(TMS)2 (100 μL, 0.10 mmol) in THF (0.5 mL) at RT. The two enantiomers were separated by Chiral chromatography (Chiracel OD).

3-(Octahydro-7-indolizinyl)-1-(2-naphthalenesulfonyl)-5-azaindole (17.5 mg, 97.7%); from 3-(octahydro-7-indolizinyl)-1-H-5-azaindole (10 mg, 0.0415 mmol), 2-naphthalenesulfonyl chloride (15 mg 0.072 mmol) and 1M NaN(TMS)2 (100 μL, 0.10 mmol) in THF (0.5 mL) at RT.

3-(Octahydro-7-indolizinyl)-2,5-dichlorobenzenesulfonyl-5-azaindole (17.5 mg, 99.8%); from 3-(octahydro-7-indolizinyl)-1-H-5-azaindole (10 mg, 0.0415 mmol), 2,5-dichlorobenzenesulfonyl chloride (15 mg, 0.061 mmol) and 1M NaN(TMS)2 (100 μL, 0.10 mmol) in THF (0.5 mL) at RT.

3-(Octahydro-7-indolizinyl)-1-benzenesulfonyl-5-azaindole (10.3 mg, 65.2%); from 3-(octahydro-7-indolizinyl)-1-H-5-azaindole (10 mg, 0.0415 mmol), benzenesulfonyl chloride (10 μL, 0.0784 mmol) and 1M NaN(TMS)2 (100 μL, 0.10 mmol) in THF (0.5 mL) at RT.

3-(Octahydro-7-indolizinyl)-1-(1-naphthalenesulfonyl)-5-azaindole (14.3 mg, 79.9%); from 3-(octahydro-7-indolizinyl)-1-H-5-azaindole (10 mg, 0.0415 mmol), 1-naphthalenesulfonyl chloride (17.2 mg, 0.0828 mmol) and 1M NaN(TMS)2 (100 μL, 0.10 mmol) in THF (0.5 mL) at RT.

3-(Octahydro-7-indolizinyl)-1-(2-naphthalenesulfonyl)-5-azaindole (10.7 mg, 59.8%); from 3-(octahydro-7-indolizinyl)-1-H-5-azaindole (10 mg, 0.0415 mmol), 2-naphthalenesulfonyl chloride (17.2 mg, 0.0828 mmol) and 1M NaN(TMS)2 (100 μL, 0.10 mmol) in THF (0.5 mL) at RT.

3-(Octahydro-7-indolizinyl)-2,5-dichlorobenzenesulfonyl-5-azaindole (12.3 mg, 70.3%); from 3-(octahydro-7-indolizinyl)-1-H-5-azaindole (10 mg, 0.0415 mmol), 2,5-dichlorobenzenesulfonyl chloride (20.3 mg, 0.0827 mmol) and 1M NaN(TMS)2 (100 μL, 0.10 mmol) in THF (0.5 mL) at RT.

1-Naphthalenesulfonyl-3-(octahydro-8-quinolizinyl)-5-azaindole (less polar isomer 71.2 mg, 37.7%) and 1-naphthalenesulfonyl-3-(octahydro-quinolizine)-5-azaindole (more polar isomer) (48.3 mg, 25.6%); from 3-(octahydro-quinolizine)-1-H-5-azaindole (102 mg, 0.42 mmol), 1-naphthalenesulfonyl chloride (176 mg, 0.84 mmol) and 1M NaN(TMS)2 (800 μL, 0.10 mmol) in THF (4 mL) at 10° C.

3-(1-Methyl-1,2,3,6-tetrahydro-4-pyridinyl)-1-benzenesulfonyl-5-azaindole (28.5 mg, 86%); from 3-(1-methyl-1,2,3,6-tetrahydro-4-pyridinyl)-5-azaindole (20 mg, 0.094 mmol), benzenesulfonyl chloride (24 μL, 0.188 mmol) and 1M NaN(TMS)2 (250 μL, 0.25 mmol) in THF (1 mL) at RT.

1-(2,6-Dichlorobenzoyl)-3-(1-methyl-1,2,3,6-tetrahydro-4-pyridinyl)-5-azaindole (34.8 mg, 96%); from 3-(1-methyl-1,2,3,6-tetrahydro-4-pyridinyl)-5-azaindole (20 mg, 0.094 mmol), 2,6-dichlorobenzoyl chloride (27 μL, 0.188 mmol) and 1M NaN(TMS)2 (250 μL, 0.25 mmol) in THF (1 mL) at RT.

3-(1-Methyl-4-piperidinyl)-1-benzenesulfonyl-5-azaindole (21.0 mg, 64%); from 3-(1-methyl-4-piperidinyl)-5-azaindole (20 mg, 0.094 mmol), benzenesulfonyl chloride (24 μL, 0.188 mmol) and 1M NaN(TMS)2 (250 μL, 0.25 mmol) in THF (1 mL) at RT.

1-(2,6-Dichlorobenzoyl)-3-(1-methyl-4-piperidinyl)-5-azaindole (8.3 mg, 23%); from 3-(1-methyl-4-piperidinyl)-5-azaindole (20 mg, 0.094 mmol), 2,6-dichlorobenzoyl chloride (27 μL, 0.188 mmol) and 1M NaN(TMS)2 (250 μL, 0.25 mmol) in THF (1 mL) at RT.

3-(Octahydro-7-indolizinyl)-1-(1-naphthalenesulfonyl)-4-azaindole (13 mg, 72.7%); from 3-(octahydro-7-indolizinyl)-1-H-4-azaindole (10 mg, 0.0415 mmol), 1-naphthalenesulfonyl chloride (17.3 mg, 0.083 mmol) and 1M NaN(TMS)2 (100 µL, 0.10 mmol) in THF (1 mL) at RT.

3-(Octahydro-7-indolizinyl)-1-(2-naphthalenesulfonyl)-4-azaindole (12.2 mg, 68.3%); from 3-(octahydro-7-indolizinyl)-1-H-4-azaindole (10 mg, 0.0415 mmol), 2-naphthalenesulfonyl chloride (17.3 mg, 0.083 mmol) and 1M NaN(TMS)2 (100 µL, 0.10 mmol) in THF (1 mL) at RT.

3-(Octahydro-7-indolizinyl)-1-(1-naphthalenesulfonyl)-4-azaindole (11 mg, 28%); from 3-(octahydro-7-indolizinyl)-1-H-4-azaindole (more polar isomer) (22 mg, 0.091 mmol), 1-naphthalenesulfonyl chloride (38 mg, 0.18 mmol) and 1M NaN(TMS)2 (200 µL, 0.10 mmol) in THF (2.5 mL) at RT.

3-(1,2,3,5,8,8a-Hexahydro-7-indolizinyl)-1-(1-naphthalenesulfonyl)-6-azaindole (8.9 mg, 43.2%); from 3-(1,2,3,5,8,8a-hexahydro-7-indolizinyl)-1H-6-Azaindole (12 mg, 0.055 mmol), 1-naphthalenesulfonyl chloride (20.9 mg, 0.1 mmol) and 1M NaN(TMS)2 (100 µL, 0.10 mmol) in THF (1 mL) at RT.

3-(Octahydro-7-indolizinyl)-1-(1-naphthalenesulfonyl)-6-azaindole (16.1 mg, 78%); from 3-(octahydro-7-indolizinyl)-1-H-4-azaindole (less polar isomer) (12 mg, 0.05 mmol), 1-naphthalenesulfonyl chloride (20.9 mg, 0.1 mmol) and 1M NaN(TMS)2 (100 µL, 0.10 mmol) in THF (1 mL) at RT.

3-(Octahydro-7-indolizinyl)-1-(1-naphthalenesulfonyl)-6-azaindole (7.8 mg, 38%); from 3-(octahydro-7-indolizinyl)-1-H-4-azaindole (more polar isomer) (12 mg, 0.05 mmol), 1-naphthalenesulfonyl chloride (20.9 mg, 0.1 mmol) and 1M NaN((TMS)2 (100 µL, 0.10 mmol) in THF (1 mL) at RT.

1-(2,6-Dichlorobenzoyl)-3-(1,2,3,5,8,8a-hexahydro-7-indolizinyl)-7-azaindole (8.8 mg, 51.1%); from 3-(1,2,3,5,8,8a-hexahydro-7-indolizinyl)-1H-7-Azaindole (10 mg, 0.0418 mmol), 2-chlorobenzoyl chloride (13 µL, 0.0907 mmol) and 1M NaN(TMS)2 (100 µL, 0.10 mmol) in THF (1 mL) at RT.

1-(2,6-Dimethoxybenzoyl)-3-(1,2,3,5,8,8a-hexahydro-7-indolizinyl)-7-azaindole (2.0 mg, 11.9%); from 3-(1,2,3,5,8,8a-hexahydro-7-indolizinyl)-1H-7-Azaindole (10 mg, 0.0418 mmol), 2,6-dimethoxybenzoyl chloride (20 mg, 0.0997 mmol) and 1M NaN(TMS)2 (100 µL, 0.10 mmol) in THF (1 mL) at RT.

1-Benzoyl-3-(1,2,3,5,8,8a-hexahydro-7-indolizinyl)-7-azaindole (8.1 mg, 58.0%); from 3-(1,2,3,5,8,8a-hexahydro-7-indolizinyl)-1H-7-Azaindole (10 mg, 0.0418 mmol), benzoyl chloride (13 µL, 0.12 mmol) and 1M NaN(TMS)2 (100 µL, 0.10 mmol) in THF (1 mL) at RT.

3-(1,2,3,5,8,8a-Hexahydro-7-indolizinyl)-1-benzenesulfonyl-7-azaindole (6.9 mg, 43.5%); from 3-(1,2,3,5,8,8a-hexahydro-7-indolizinyl)-1H-7-Azaindole (10 mg, 0.0418 mmol), benzenesulfonyl chloride (20 mg, 0.113 mmol) and 1M NaN(TMS)2 (100 µL, 0.10 mmol) in THF (0.5 mL) at RT.

1-(4-Fluorobenzenesulfonyl)-3-(1,2,3,5,8,8a-hexahydro-7-indolizinyl)-7-azaindole (9.1 mg, 54.8%); from 3-(1,2,3,5,8,8a-hexahydro-7-indolizinyl)-1H-7-Azaindole (10 mg, 0.0418 mmol), 4-fluorobenzenesulfonyl chloride (20 mg, 0.103 mmol) and 1M NaN(TMS)2 (100 µL, 0.10 mmol) in THF (0.5 mL) at RT.

1-(4-Chlorobenzenesulfonyl)-3-(1,2,3,5,8,8a-hexahydro-7-indolizinyl)-7-azaindole (10.2 mg, 58.9%); from 3-(1,2,3,5,8,8a-hexahydro-7-indolizinyl)-1H-7-Azaindole (10 mg, 0.0418 mmol), 4-fluorobenzenesulfonyl chloride (20 mg, 0.095 mmol) and 1M NaN(TMS)2 (100 µL, 0.10 mmol) in THF (0.5 mL) at RT.

3-(1,2,3,5,8,8a-Hexahydro-7-indolizinyl)-1-(4-methyl-benzenesulfonyl)-7-azaindole (6.9 mg, 42.0%); from 3-(1,2,3,5,8,8a-hexahydro-7-indolizinyl)-1H-7-Azaindole (10 mg, 0.0418 mmol), 4-methyl-benzenesulfonyl chloride (20 mg, 0.105 mmol) and 1M NaN(TMS)2 (100 µL, 0.10 mmol) in THF (0.5 mL) at RT.

3-(1,2,3,5,8,8a-Hexahydro-7-indolizinyl)-1-(1-naphthalenesulfonyl)-7-azaindole (8.4 mg, 46.8%); from 3-(1,2,3,5,8,8a-hexahydro-7-indolizinyl)-1H-7-Azaindole (10 mg, 0.0418 mmol), 1-naphthalenesulfonyl chloride (20 mg, 0.088 mmol) and 1M NaN(TMS)2 (100 µL, 0.10 mmol) in THF (0.5 mL) at RT.

3-(1,2,3,5,8,8a-Hexahydro-7-indolizinyl)-1-(2-naphthalenesulfonyl)-7-azaindole (9.4 mg, 52.4%); from 3-(1,2,3,5,8,8a-hexahydro-7-indolizinyl)-1H-7-Azaindole (10 mg, 0.0418 mmol), 2-naphthalenesulfonyl chloride (20 mg, 0.088 mmol) and 1M Na((TMS)2 (100 µL, 0.10 mmol) in THF (0.5 mL) at RT.

3-(Octahydro-7-indolizinyl)-1-benzenesulfonyl-7-azaindole (14.4 mg, 91.1%); from 3-(octahydro-7-indolizinyl)-1H-7-azaindole (less polar isomer) (10 mg, 0.0415 mmol), benzenesulfonyl chloride (10 µL, 0.0784 mmol) and 1M NaN(TMS)2 (100 µL, 0.10 mmol) in THF (0.5 mL) at RT.

3-(Octahydro-7-indolizinyl)-1-(1-naphthalenesulfonyl)-7-azaindole (17.8 mg, 99%); from 3-(octahydro-7-indolizinyl)-1-H-5-azaindole (less polar isomer) (10 mg, 0.0415 mmol), 1-naphthalenesulfonyl chloride (17.2 mg, 0.0828 mmol) and 1M NaN(TMS)2 (100 µL, 0.10 mmol) in THF (0.5 mL) at RT.

3-(Octahydro-7-indolizinyl)-1-(2-naphthalenesulfonyl)-7-azaindole (15.3 mg, 85.5%); from 3-(octahydro-7-indolizinyl)-1-H-5-azaindole (less polar isomer) (10 mg, 0.0415 mmol), 2-naphthalenesulfonyl chloride (17.2 mg, 0.0828 mmol) and 1M NaN(TMS)$_2$ (100 µL, 0.10 mmol) in THF (0.5 mL) at RT.

3-(Octahydro-7-indolizinyl)-2,5-dichlorobenzenesulfonyl-5-azaindole (14.2 mg, 81%); from 3-(octahydro-7-indolizinyl)-1-H-5-azaindole (less polar isomer) (10 mg, 0.0415 mmol), 2,5-dichlorobenzenesulfonyl chloride (20.3 mg, 0.0827 mmol) and 1M NaN(TMS)$_2$ (100 µL, 0.10 mmol) in THF (0.5 mL) at RT.

3-(Octahydro-7-indolizinyl)-1-(1-naphthalenesulfonyl)-7-azaindole (9.1 mg, 50.8%); from 3-(octahydro-7-indolizinyl)-1-H-5-azaindole (more polar isomer) (8 mg, 0.033 mmol), 1-naphthalenesulfonyl chloride (15 mg, 0.072 mmol) and 1M NaN(TMS)$_2$ (100 µL, 0.10 mmol) in THF (0.5 mL) at RT.

3-(Octahydro-7-indolizinyl)-1-(2-naphthalenesulfonyl)-7-azaindole (9.4 mg, 85.5%); from 3-(octahydro-7-indolizinyl)-1-H-5-azaindole (more polar isomer) (8 mg, 0.033 mmol), 2-naphthalenesulfonyl chloride (15 mg, 0.072 mmol) and 1M NaN(TMS)$_2$ (100 µL, 0.10 mmol) in THF (0.5 mL) at RT.

Example 3

3-(1-Methyl-1,2,3,6-tetrahydro-4-pyridinyl)-1-benzenesulfonyl-7-azaindole

Sodium bis(trimethylsilyl)amide (0.2 mL, 1M in THF, 0.23 mmol) was added to a solution of 3-(1-methyl-1,2,3,6-tetrahydro-4-pyridinyl)-7-azaindole (24.9 mg, 0.12 mmol) in THF (2.5 mL) at −78° C. and the mixture stirred for 1 h. Benzenesulfonyl chloride (30 µL, 0.24 mmol) was added and the mixture stirred at room temperature for 2 h, prior to quenching with water (4 drops) and silica gel (.about. 1 g). Purification using solid phase extraction tubes (1000 mg silica, eluting with 0-10% 2M methanolic ammonia in dichloromethane) yielded 3-(1-methyl-1,2,3,6-tetrahydro-4-pyridinyl)-1-benzenesulfonyl-7-azaindole (21.3 mg, 51%, HRMS-FAB+ for C$_9$H$_9$NOS: calculated MH+: 354.12762. Found: 354.12896).

In a like manner, the following additional compounds were prepared:

1-(4-Methoxybenzenesulfonyl)-3-(1-methyl-1,2,3,6-tetrahydro-4-pyridinyl)-7-azaindole; (24.1 mg, 54%); from 3-(1-methyl-1,2,3,6-tetrahydro-4-pyridinyl)-1H-7-azaindole (24.9 mg, 0.12 mmol) and 4-methoxybenzenesulfonyl chloride (48.2 mg, 0.23 mmol); HRMS-FAB$_+$ for C$_{20}$H$_{21}$N$_3$O$_3$S: calculated MH+: 384.13818. Found: 384.13811.

1-(4-Fluorobenzenesulfonyl)-3-(1-methyl-1,2,3,6-tetrahydro-4-pyridinyl)-7-azaindole; (21.1 mg, 48%); from 3-(1-methyl-1,2,3,6-tetrahydro-4-pyridinyl)-1H-7-azaindole (24.9 mg, 0.12 mmol) and 4-fluorobenzenesulfonyl chloride (47 mg, 0.24 mmol); HRMS-FAB+ for C19H$_{18}$N$_3$O$_2$SF: calculated MH+: 372.11819. Found: 372.11690.

1-Benzoyl-3-(1-methyl-1,2,3,6-tetrahydro-4-pyridinyl)-7-azaindole; (6.7 mg, 18%); from 3-(1-methyl-1,2,3,6-tetrahydro-4-pyridinyl)-1H-7-azaindole (25.0 mg, 0.12 mmol) and benzoyl chloride (28 µL, 0.24 mmol); HRMS-FAB+ for C$_{20}$H$_{19}$N$_3$O: calculated MH+: 318.16064. Found: 318.16191.

1-(4-Methoxybenzoyl)-3-(1-methyl-1,2,3,6-tetrahydro-4-pyridinyl)-7-azaindole; (16.4 mg, 41%); from 3-(1-methyl-1,2,3,6-tetrahydro-4-pyridinyl)-1H-7-azaindole (24.8 mg, 0.12 mmol) and 4-methoxybenzoyl chloride (35 µL, 0.24 mmol); HRMS-FAB+ for C$_{21}$H$_{21}$N$_3$O$_2$5 calculated MH+: 348.17120. Found: 348.16994.

1-(4-Fluorobenzoyl)-3-(1-methyl-1,2,3,6-tetrahydro-4-pyridinyl)-7-azaindole; (10.1 mg, 26%); from 3-(1-methyl-1,2,3,6-tetrahydro-4-pyridinyl)-1H-7-azaindole (24.8 mg, 0.12 mmol) and 4-fluorobenzoyl chloride (28 µL, 0.24 mmol); HRMS-FAB+ for C$_{20}$H$_{18}$N$_3$OF: calculated MH+: 336.15121. Found: 336.15100.

Example 4

3-(Octahydro-7-indolizinyl)-1H-5-Azaindole

A mixture of 3-(1,2,3,5,8,8a-hexahydro-7-indolizinyl)-1H-5-Azaindole (400 mg, 1.67 mmol) and 10% Pd/C (400 mg) in ethanol (15 mL) was stirred under Hxxx2 overnight. The reaction mixture was filtered and the filtrate concentrated and purified by column chromatography. Elution with 5% methanol (2M/NH$_3$) in dichloromethane gave the less polar isomer (297.7 mg, 73.5%) and with 10% methanol (2M/NH$_3$) in dichloromethane gave the more polar isomer (73 mg, 18.1%).

In a similar fashion, the following compounds were prepared:

3-(Octahydro-quinolizine)-1H-5-Azaindole (95.5 mg, 79%); from 3-(1,2,4,6,7,9a-hexahydro-2H-quinolizine-2-yl)-5-azaindole (120 mg, 0.474 mmol) and 10% Pd/C (120 mg) in ethanol (2 mL) under H$_2$ overnight.

3-(1-Methyl-4-piperidinyl)-5-azaindole (0.557 g, 76%); from 3-(1-methyl-1,2,3,6-tetrahydro-4-pyridinyl)-5-azaindole (0.725 g, 3.4 mmol) and 10% Pd/C (0.45 g, 2.04 mmol) in ethanol (8 mL) under H$_2$ overnight.

3-(Octahydro-7-indolizinyl)-1H-4-azaindole (less polar isomer 378 mg, 75%; and more polar isomer 111 mg, 22%) from 3-(1,2,3,5,8,8a-hexahydro-7-indolizinyl)-4-azaindole (500 mg, 2.1 mmol) and 10% Pd/C (290 mg) in ethanol (10 mL) under H$_2$ overnight.

3-(Octahydro-7-indolizinyl)-1H-6-azaindole (less polar isomer 87 mg, 72%; and more polar isomer 34 mg, 28%); from 3-(1,2,3,5,8,8a-hexahydro-7-indolizinyl)-6-azaindole (120 mg, 0.5 mmol) and 10% Pd/C (100 mg) in ethanol (2 mL) under H$_2$ overnight.

3-(Octahydro-7-indolizinyl)-1H-7-azaindole (less polar isomer 134.2 mg, 49.5% and more polar isomer 36.6 mg, 13.3%); from 3-(1,2,3,5,8,8a-hexahydro-7-indolizinyl)-6-azaindole (270 mg, 1.13 mmol) and 10% Pd/C (300 mg) in ethanol (4 mL) under H$_2$ overnight.

Example 4

Binding Affinity for the 5-HT$_6$ Receptor

All of the compounds of the invention were evaluated using cell types receptive specifically to the 5-HT$_6$ receptor (for cloning and characterization of the human 5-HT$_6$ receptor see Kohen, et al. J. Neurochemistry, 66, 1996: 47-56). The assay protocol generally entailed the incubation of membranes prepared from cells expressing the 5-HT$_6$ receptor with $^3$H-LSD (2 nM). Increasing levels of the test compound were incubated with the radioligand and the membrane homogenates prepared from the recombinant cells. After a 60 minute incubation at 37° C., the incubation was terminated by vacuum filtration. The filters were washed with buffer and the filters were counted for radioactivity using liquid scintillation spectrometry. The affinity of the test compound for the 5-HT$_6$ receptor was determined by computer-assisted analysis of the data and determining the amount of the compound necessary to inhibit 50% of the binding of the radioligand to the receptor. Concentrations ranging from $10^{-11}$ M to $10^{-5}$ M of the test compound were evaluated. For comparison, the affinity of clozapine (Ki=3 nM) for the 5-HT$_6$ receptor was used as a standard. Affinity for the 5-HT$_6$ receptor is expressed as the amount (in percent) of binding of the radioligand that is inhibited in the presence of 100 nM of test compound. A greater percent inhibition indicates greater affinity for the 5-HT$_6$ receptor.

Selected compounds of the invention showed an percent inhibition of greater than 50% for the 5-HT$_6$ receptor.

Specific compounds of the invention, for example 1-(1-Naphthalenesulfonyl)-3-(octahydro-7-indolizinyl)-4-azaindole; 1-(1-Naphthalenesulfonyl)-3-(octahydro-8-quinolizinyl)-5-azaindole (from more polar isomer); 1-(1-Naphthalenesulfonyl)-3-(octahydro-7-indolizinyl)-6-azaindole (less polar isomer) and 1-(2-Naphthalenesulfonyl)-3-(octahydro-7-indolizinyl)-7-azaindole (from more polar isomer) showed a percent inhibition of greater than 80% for the 5-HT$_6$ receptor.

More specific compounds of the invention, for example, 1-(2-Naphthalenesulfonyl)-3-(octahydro-7-indolizinyl)-4-azaindole; 3-(1,2,3,5,8,8a-Hexahydro-7-indolizinyl)-1-(1-naphthalenesulfonyl)-5-azaindole; 1-(1-Naphthalenesulfonyl)-3-(octahydro-7-indolizinyl)-6-azaindole (less polar isomer); and 1-(2-Naphthalenesulfonyl)-3-(octahydro-7-indolizinyl)-7-azaindole (from more polar isomer) showed a percent inhibition of greater than 95% for the 5-HT$_6$ receptor.

In terms of selectivity, selected compounds of the invention showed an percent inhibition of greater than 50% for the 5-HT$_6$ receptor and also had a percent inhibition less than 50% for other serotonin receptors, specifically the 5-HT$_{2A}$, 5HT$_{2C}$ and 5-HT$_7$ receptors.

Specific compounds, for example 3-(1,2,3,5,8,8a-Hexahydro-7-indolizinyl)-1-(4-methylbenzenesulfonyl)-5-azaindole; 1-(1-Naphthalenesulfonyl)-3-(octahydro-7-indolizinyl)-6-azaindole (more polar isomer) and 1-(2,6-Dichlorobenzoyl)-3-(1,2,3,5,8,8a-hexahydro-7-indolizinyl)-

7-azaindole showed a percent inhibition of greater than 80% for the 5-HT$_6$ receptor and less than 20% for the 5-HT$_{2A}$, 5HT$_{2C}$ and 5-HT$_7$ receptors.

More specific compounds, for example 1-(1-Naphthalenesulfonyl)-3-(octahydro-7-indolizinyl)-4-azaindole (more polar isomer); 3-(1,2,3,5,8,8a-Hexahydro-7-indolizinyl)-1-benzenesulfonyl-5-azaindole and 3-(1,2,3,5,8,8a-Hexahydro-7-indolizinyl)-1-(2-naphthalenesulfonyl)-7-azaindole showed a percent inhibition of greater than 90% for the 5-HT$_6$ receptor and less than 10% for the 5-HT$_{2A}$, 5HT$_{2C}$ and 5-HT$_7$ receptors.

Example 5

Functional Assay

The 5HT$_6$ receptor responds to serotonin and other agonists by increasing adenyl cyclase mediated production of cyclic AMP. Particular test compounds were assayed for their effect on adenyl cyclase activity using the procedure described below.

Compounds acting as antagonists at the 5HT$_6$ receptor will antagonize the agonist effect of serotonin and thus, will block the serotonin-induced increase in adenyl cyclase activity.

HEK 293 cells stably expressing the human 5HT$_6$ receptor were plated in 6 well plates in DMEM (Dulbecco's Modified Eagle Medium)/F12 (Nutrient Mixture F12-Ham) media with 10% FCS (fetal calf serum) and G418 (Geneticen Disulfate, 500 ug/ml), and incubated at 37° C. in a CO$_2$ incubator. The cells were allowed to grow to about 70% confluence before use in the assay.

The culture medium of each well was removed, and the wells were washed once with serum free media. Then 2 ml of SFM+IBMX medium (SFM with 0.5 mM IBMX, 3-isobutyl-1-methylxanthine, 0.1% ascorbic acid and 10 mM pargyline) was added to each well and the wells were incubated at 37° C. for 10 min. Following incubation, the SFM+IBMX medium was removed from each well and fresh SFM+IBMX media was added to the wells separately with one of a) serotonin (1 µM final concentration); b) test compound (100 nM and 10 µM, to test for agonist activity); and c) test compound (100 nM and 10 µM) along with serotonin (µM final concentration, to test for antagonist activity). Basal adenyl cyclase activity was determined from wells with only SFM+IBMX media added.

The cells were then incubated at 37° C. for 30 minutes in a COxxx2 incubator. Following incubation, the media were removed from each well. The wells were washed once with 1 ml of PBS (phosphate buffered saline). Each well was then treated with 1 mL cold 95% ethanol:5 mM EDTA (2:1) at 4° C. for 1 hour. The cells from each well were then scraped and transferred into individual Eppendorf tubes. The tubes were centrifuged for 5 minutes at 4° C., and the supernatants were transferred to new Eppendorf tubes and stored at 4° C. The pellets were discarded and the supernatants were stored at 4° C. until assayed for cAMP concentration. cAMP content for each extract was determined in duplicate by EIA (enzyme-immunoassay) using the Amersham Biotrak cAMP EIA kit (Amersham RPN 225). Final results were expressed as % basal response for agonists and % reversal of serotonin response for antagonists.

The total stimulation of adenyl cyclase by serotonin (Sxxxo) was determined as the difference in concentration of cAMP in the serotonin-treated cells (C$_d$) and the basal-treated cells (C$_f$).

$$S_o = C_f - C_d$$

The net stimulation (S) of basal adenyl cyclase by an agonist test compound was determined as the difference in cAMP concentration in the drug-treated cell (C) and the basal-treated cells (C$_s$).

$$S = C_f - C$$

The net stimulation (S$_s$) of basal adenyl cyclase by serotonin in the presence of an antagonist test compound was determined as the difference in cAMP concentration in the seronton in-drug-treated cells (C$_s$) and the basal-treated cells (C$_f$).

$$S_s = C_f - C_s$$

The ability of the antagonist test compound to reverse the serotonin stimuation of adenyl cyclase activity (% reversal, % R) was determined by the formula:

$$\% R = (1 - S_s/S_o) \times 100$$

Selected compounds of the invention, for example 1-(benzenesulfonyl)-3-(1,2,3,5,8,8a-Hexahydro-7-indolizinyl)-5-azaindole; 1-(benzenesulfonyl)-3-(1,2,3,5,8,8a-Hexahydro-7-indolizinyl)-7-azaindole; 3-(1,2,3,5,8,8a-Hexahydro-7-indolizinyl)-1-(1-naphthalenesulfonyl)-5-azaindole and 3-(1,2,3,5,8,8a-Hexahydro-7-indolizinyl)-1-(1-naphthalenesulfonyl)-7-azaindole, were able to reverse the serotonin stimulation of adenyl cyclase and thus were shown to behave as a 5-HT$_6$ receptor antagonists.

We claim:

1. A method of treating Alzheimer's disease in a patient in need thereof, comprising administering to the patient a pharmaceutical composition comprising a compound of Formula (I), or a pharmaceutically acceptable salt thereof:

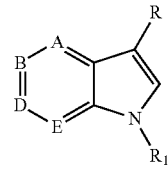

Formula I

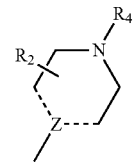

Formula II

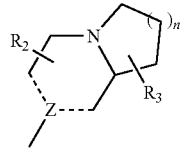

Formula III wherein:
R represents a group of Formula II or Formula III;
one of A, B, D or E is a N atom, the remainder being CH groups;
$R_1$ is selected from the group consisting of SO$_2$Ar, C(O)Ar, CH$_2$Ar and Ar;
$R_2$, $R_3$ and $R_4$ are independently selected from the group consisting of H and alkyl;
---- represents a single or double bond, with the proviso that there is only one double bond in the ring at a time;

n is an integer of from 1-3;

Z is selected from the group consisting of C, CH and N, provided that when ---- is a double bond, Z is C and when ---- is a single bond, Z is selected from CH and N; and Ar is an optionally substituted aryl group;

with the proviso that when R is a group of Formula II, $R_1$ is $SO_2Ar$.

2. The method of claim 1, wherein the pharmaceutical composition comprises a pharmaceutically acceptable carrier.

3. The method of claim 1, wherein 0.1 to 50 mg of the compound of formula I is administered.

4. The method of claim 2, wherein the pharmaceutical composition is administered orally.

5. The method of claim 4, wherein the pharmaceutically acceptable carrier is magnesium stearate, starch, lactose, sucrose, or cellulose.

6. The method of claim 2, wherein the pharmaceutical composition is administered parenterally.

7. The method of claim 6, wherein the pharmaceutically acceptable carrier is polyethylene glycol, polyvinyl pyrrolidone, lecithin, arachis oil, or sesame oil.

8. The method of claim 1, wherein the compound according to Formula (I) shows greater than 80% inhibition for the $5\text{-}HT_6$ receptor.

9. The method of claim 8, wherein the compound according to Formula (I) shows less than 20% inhibition for the $5\text{-}HT_{2A}$, $5HT_{2c}$ and $5\text{-}HT_7$ receptors.

10. A method of treating Alzheimer's disease in a patient in need thereof comprising administering to the patient a pharmaceutical composition comprising a compound according to Formula (V), or a pharmaceutically acceptable salt thereof:

Formula V wherein:
one of A, B, D or E is a N atom, the remainder being CH groups;

$R_1$ is $SO_2Ar$;

$R_2$ and $R_4$ are independently selected from the group consisting of H and alkyl;

---- represents a single or double bond, with the proviso that there is only one double bond in the ring at a time;

Z is selected from the group consisting of C, CH and N, provided that when ---- is a double bond, Z is C and when ---- is a single bond, Z is selected from CH and N; and Ar is an optionally substituted aryl group.

11. The method of claim 10, wherein the pharmaceutical composition comprises a pharmaceutically acceptable carrier.

12. The method of claim 10, wherein 0.1 to 50 mg of the compound of formula V is administered.

13. The method of claim 1, wherein the compound of Formula (I) is selected from the group consisting of:
1-(2,6-Dichlorobenzoyl)-3-(1,2,3,5,8,8a-hexahydro-7-indolizinyl)-1H-5-azaindole;
1-(2,6-Dichlorobenzoyl)-3-(1,2,3,5,8,8a-hexahydro-7-indolizinyl)-1H-7-azaindole;
1-(2,6-Dichlorobenzoyl)-3-(1-methyl-1,2,3,6-tetrahydro-4-pyridinyl)-1H-5-azaindole;
1-(2,6-Dichlorobenzoyl)-3-(1-methyl-4-piperidinyl)-1H-5-azaindole;
1-(2,6-Dimethoxylbenzoyl)-3-(1,2,3,5,8,8a-hexahydro-7-indolizinyl)-1H-5-azaindole;
1-(2,6-Dimethoxylbenzoyl)-3-(1,2,3,5,8,8a-hexahydro-7-indolizinyl)-1H-7-azaindole;
1-(2-Chlorobenzoyl)-3-(1,2,3,5,8,8a-hexahydro-7-indolizinyl)-1H-5-azaindole;
1-(4-Fluorobenzoyl)-3-(1-methyl-1,2,3,6-tetrahydro-4-pyridinyl)-1H-7-azaindole;
1-(4-Methoxybenzoyl)-3-(1-methyl-1,2,3,6-tetrahydro-4-pyridinyl)-1H-7-azaindole;
1-Benzoyl-3-(1,2,3,5,8,8a-hexahydro-7-indolizinyl)-1H-5-azaindole;
1-Benzoyl-3-(1,2,3,5,8,8a-hexahydro-7-indolizinyl)-1H-7-azaindole;
1-Benzoyl-3-(1-methyl-1,2,3,6-tetrahydro-4-pyridinyl)-1H-7-azaindole;
or a pharmaceutically acceptable salt thereof.

14. The method of claim 1, wherein the compound of Formula (I) is selected from the group consisting of:
1-(4-Chlorobenzenesulfonyl)-3-(1,2,3,5,8,8a-hexahydro-7-indolizinyl)-1H-7-azaindole;
1-(4-Chlorobenzenesulfonyl)-3-(1,2,3,5,8,8a-hexahydro-7-indolizinyl)-1H-5-azaindole;
1-(4-Fluorobenzenesulfonyl)-3-(1,2,3,5,8,8a-hexahydro-7-indolizinyl)-1H-7-azaindole;
1-(4-Fluorobenzenesulfonyl)-3-(1,2,3,5,8,8a-hexahydro-7-indolizinyl)-1H-5-azaindole;
1-(4-Fluorobenzenesulfonyl)-3-(1-methyl-1,2,3,6-tetrahydro-4-pyridinyl)-1H-7-azaindole;
1-(4-Methoxybenzenesulfonyl)-3-(1-methyl-1,2,3,6-tetrahydro-4-pyridinyl)-1H-7-azaindole;
3-(1,2,3,5,8,8a-Hexahydro-7-indolizinyl)-1-(4-methylbenzenesulfonyl)-1H-7-azaindole;
3-(1,2,3,5,8,8a-Hexahydro-7-indolizinyl)-1-(4-methylbenzenesulfonyl)-1H-5-azaindole;
or a pharmaceutically acceptable salt thereof.

15. The method of claim 1, wherein the compound of Formula (I) is selected from the group consisting of:
3-(1,2,3,5,8,8a-Hexahydro-7-indolizinyl)-1-benzenesulfonyl-1H-5-azaindole;
3-(1,2,3,5,8,8a-Hexahydro-7-indolizinyl)-1-benzenesulfonyl-1H-7-azaindole;
3-(1-Methyl-1,2,3,6-tetrahydro-4-pyridinyl)-1-benzenesulfonyl-1H-5-azaindole;
3-(1-Methyl-1,2,3,6-tetrahydro-4-pyridinyl)-1-benzenesulfonyl-1H-7-azaindole;
3-(1-Methyl-4-piperidinyl)-1-benzenesulfonyl-1H-5-azaindole;
3-(Octahydro-7-indolizinyl)-1-benzenesulfonyl-1H-5-azaindole;
3-(Octahydro-7-indolizinyl)-1-benzenesulfonyl-1H-7-azaindole;
3-(Octahydro-7-indolizinyl)-2,5-dichlorobenzenesulfonyl-1H-5-azaindole;
or a pharmaceutically acceptable salt thereof.

16. The method of claim 1, wherein the compound of Formula (I) is selected from the group consisting of:
- 1-(1-Naphthalenesulfonyl)-3-(octahydro-4-quinolizinyl)-1H-5-azaindole;
- 3-(1,2,3,5,8,8a-Hexahydro-7-indolizinyl)-1-(1-naphthalenesulfonyl)-1H-6-azaindole;
- 3-(1,2,3,5,8,8a-Hexahydro-7-indolizinyl)-1-(1-naphthalenesulfonyl)-1H-7-azaindole;
- 3-(1,2,3,5,8,8a-Hexahydro-7-indolizinyl)-1-(1-naphthalenesulfonyl)-1H-5-azaindole;
- 3-(1,2,3,5,8,8a-Hexahydro-7-indolizinyl)-1-(2-naphthalenesulfonyl)-1H-5-azaindole;
- 3-(1,2,3,5,8,8a-Hexahydro-7-indolizinyl)-1-(2-naphthalenesulfonyl)-1H-7-azaindole;
- 3-(Octahydro-7-indolizinyl)-1-(1-naphthalenesulfonyl)-1H-4-azaindole;
- 3-(Octahydro-7-indolizinyl)-1-(1-naphthalenesulfonyl)-1H-5-azaindole;
- 3-(Octahydro-7-indolizinyl)-1-(1-naphthalenesulfonyl)-1H-6-azaindole;
- 3-(Octahydro-7-indolizinyl)-1-(1-naphthalenesulfonyl)-1H-7-azaindole;
- 3-(Octahydro-7-indolizinyl)-1-(2-naphthaleriesulfonyl)-1H-4-azaindole;
- 3-(Octahydro-7-indolizinyl)-1-(2-naphthalenesulfonyl)-1H-5-azaindole;
- 3-(Octahydro-7-indolizinyl)-1-(2-naphthalenesulfonyl)-1H-7-azaindole;

or a pharmaceutically acceptable salt thereof.

* * * * *